(12) United States Patent
Lee et al.

(10) Patent No.: US 7,344,858 B2
(45) Date of Patent: Mar. 18, 2008

(54) GLYCOSYLATED HUMAN GRANULOCYTE COLONY-STIMULATING FACTOR (G-CSF) ISOFORM

(75) Inventors: Eun Jung Lee, Gyeonggi-do (KR); Hyun Seok Kim, Seoul (KR); Jong Sang Chung, Seoul (KR); Ki Wan Kim, Seoul (KR); Yeon Hyang Kim, Seoul (KR); Hyune Soo Lee, Seoul (KR); Hyung Kon Koh, Seoul (KR); Myung Suk Oh, Gyeonggi-do (KR)

(73) Assignee: CJ Corp, Seoul (KR)

( * ) Notice: Subject to any disclaimer, the term of this patent is extended or adjusted under 35 U.S.C. 154(b) by 519 days.

(21) Appl. No.: 10/651,395

(22) Filed: Aug. 29, 2003

(65) Prior Publication Data

US 2004/0082038 A1  Apr. 29, 2004

(30) Foreign Application Priority Data

Aug. 31, 2002  (KR) .................... 10-2002-0052364

(51) Int. Cl.
  *C12N 15/27* (2006.01)
  *C12N 15/66* (2006.01)
  *C07K 14/535* (2006.01)
  *A61K 38/18* (2006.01)

(52) U.S. Cl. ............... 435/69.1; 435/320.1; 536/23.1; 536/23.5; 530/350; 530/351; 514/2; 514/8; 514/12

(58) Field of Classification Search .............. None
See application file for complete search history.

(56) References Cited

U.S. PATENT DOCUMENTS

| 5,217,881 A | * | 6/1993 | Park ..................... 435/69.5 |
| 5,298,395 A | * | 3/1994 | Park ..................... 435/7.21 |
| 5,756,349 A | | 5/1998 | Lin ...................... 435/325 |
| 2004/0254351 A1 | * | 12/2004 | Beals et al. ............. 530/351 |

OTHER PUBLICATIONS

Hübel et al., 2003, Ann. Hematol. 82 :207-213.*
Basu et al., 2002, Int. J. Mol. Med. 10:3-10.*
Takashi Kuwabara, et al., *Pharmacokinetics and Pharmacodynamics of a Recombinant Human Granulocyte Colony-Stimulating Factor*, Drug Metabolism Reviews, 28(4), pp. 625-658, (1996).
Masayoshi Oh-Eda, et al., *O-Linked Sugar Chain of Human Granulocyte Colony-stimulating Factor Protects It Against Polymerization and Denaturation Allowing It to Retain Its Biological Activity*, The Journal of Biological Chemistry, vol. 265, No. 20, Jul. 15, 1990, pp. 11432-11435.

(Continued)

*Primary Examiner*—Elizabeth C. Kemmerer
(74) *Attorney, Agent, or Firm*—Hunton & Williams

(57) ABSTRACT

Disclosed are human G-CSF isoforms having a modified amino acid sequence containing a glycosylation sequence Asn-X-Ser/Thr (N-X-S/T) at one or more specific amino acid positions according to the present invention, genes encoding the human G-CSF isoforms, and expression vectors carrying the genes, eukaryotic cells transformed or transfected with the expression vectors. Also, the present invention discloses a method of preparing a glycosylated human G-CSF isoform, comprising the steps of culturing the transformant or transfectant and isolating a glycosylated human G-CSF isoform from the culture supernatant or cell lysates, a human G-CSF isoform prepared by the method, and a pharmaceutical composition comprising the human G-CSF isoform.

4 Claims, 9 Drawing Sheets

OTHER PUBLICATIONS

Brian I. Lord, et al., *Kinetics of Neutrophil Production in Normal and Neutropenic Animals During the Response to Filgrastim (r-metHu G-CSF) or Filgrastim SD/01 (PEG-r-metHu G-CSF)*, Clinical Cancer Research, vol. 7, Jul. 2001, pp. 2085-2090.

Graham Molineaux, et al., *A New Form or Filgrastim with Sustained Duration in Vivo and Enhanced Ability to Mobilize PBPC in Both Mice and Humans*, Experimental Hematology 27 (1999), pp. 1724-1734.

Belinda R. Avalos, *Molecular Analysis of the Granulocyte Colony-Stimulating Factor Receptor*, The Journal of The American Society of Hematology, vol. 88, No. 3, Aug. 1, 1996, pp. 761-777.

Judith E. Layton, et al., *Identification of Ligand-Binding Site III on the Immunoglobulin-Like Domain of the Granulocyte Colony-Stimulating Factor Receptor*, The Journal of Biological Chemistry, vol. 276, No. 39, Sep. 28, 2001, pp. 36779-36787.

Osamu Hiraoka, et al., *Requirement for the Immunoglobulin-Like Domain of Granulocyte Colony-Stimulating Factor Receptor in Formation of a 2:1 Receptor-Ligand Complex*, The Journal of Biological Chemistry, vol. 270, No. 43, Oct. 27, 1995, pp. 25928-25934.

Judith E. Layton, et al., *Interaction of Granulocyte Colony-Stimulating Factor (G-CSF) With Its Receptor*, The Journal of Biological Chemistry, vol. 274, No. 25, Jun. 18, 1999, pp. 17445-17451.

\* cited by examiner

Fig. 1

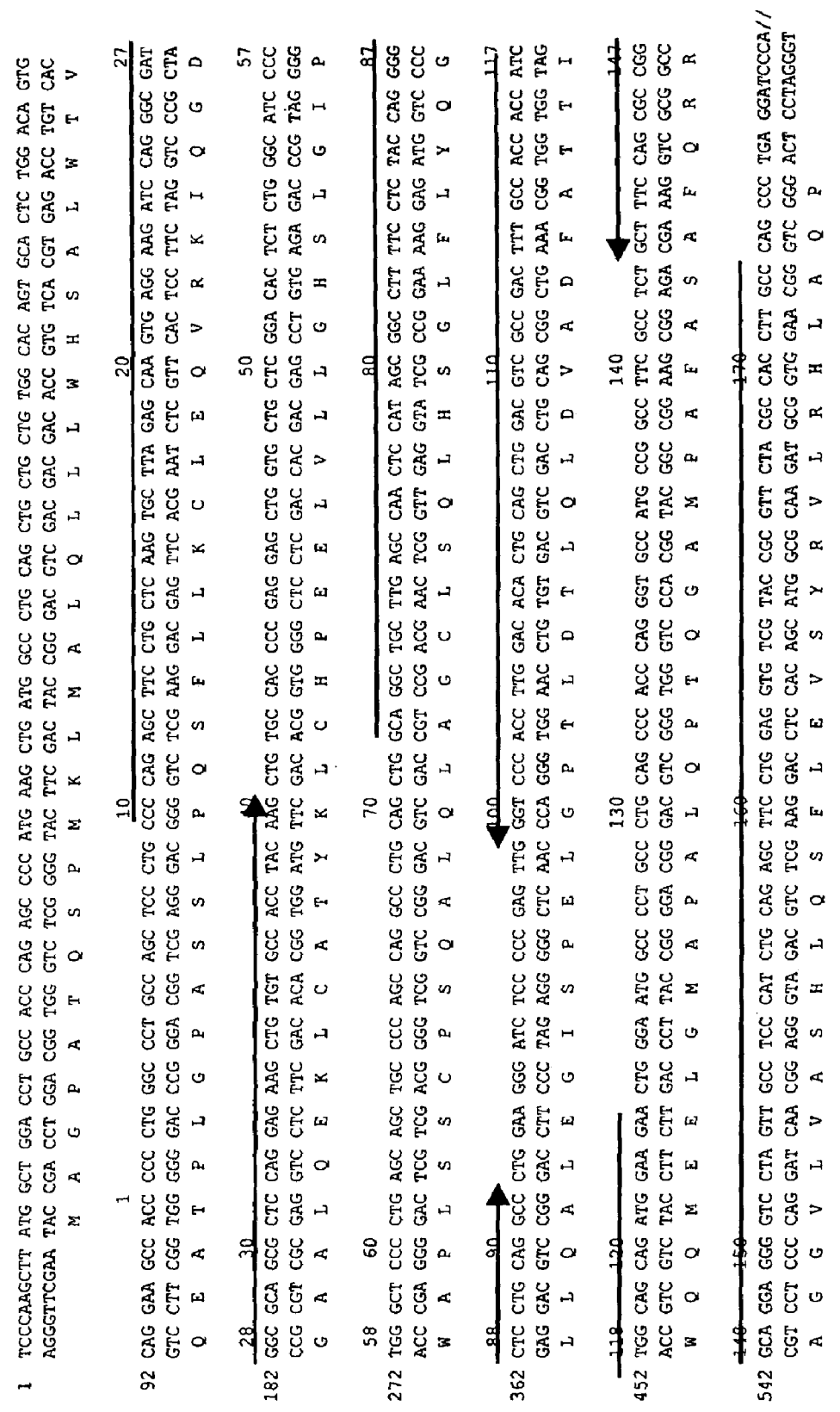

```
1   TCCCAAGCTT ATG GCT GGA CCT GCC ACC CAG AGC CCC ATG AAG CTG ATG GCC CTG CAG CTG CTG TGG CAC AGT GCA CTC TGG ACA GTG
    AGGGTTCGAA TAC CGA CCT GGA CGG GTC TCG GGG TAC TTC GAC TAC CGG GAC GTC GAC GAC ACC GTG TCA CGT GAG ACC TGT CAC
                M   A   G   P   A   T   Q   S   P   M   K   L   M   A   L   Q   L   L   W   H   S   A   L   W   T   V
                                                                                                                                    27
92  CAG GAA GCC ACC CCC CTG GGC CCT GCC CCT CGG GGA CCG GTC TCG AGG GTC TGG CCC CAG AGC TTC CTG CTC AAG TGC TTA GAG GTC CAA GTG AGG AAG ATC CAG GGC GAT
    GTC CTT CGG TGG GGG GAC CCG GGA CGG GGA GCC CCT GGC CAG AGC TCC AGA CCG GGT CTC GAA GGA CGA GTT CAC GAA CTC ACG AAT CTC CAG GTT CAC TCC TTC GTC CCG CTA
    Q   E   A   T   P   L   G   P   A   P   R   G   P   V   S   R   V   W   P   Q   S   F   L   L   K   C   L   E   Q   V   R   K   I   Q   G   D
        28                                  30                                                          40                                          50                              57
182 GGC GCA GCG CTC CAG GAG GAA CTG TGT GCC TAC ACC AAG CTG GAG GAG CTG TGC CAC CCC GAG GAG CTG GTG CTC CTG GGA CAC TCT CTG GGC ATC CCC
    CCG CGT CGC GAG GTC CTC CTT GAC ACA CGG ATG TGG TTC GAC CTC CTC GAC ACG CGG GGG CTC CTC GAC CAC GAG GAC CCT GTG AGA CCG TAG GGG
    G   A   A   L   Q   E   E   L   C   A   Y   T   K   L   E   E   L   C   H   P   E   E   L   V   L   L   G   H   S   L   G   I   P
        58                              60                                                  70                                                  80                          87
272 TGG GCT CCC CTG AGC GCC AGC TGC CCC AGC CTG GCA GGC CTG GAC CTG CTT GAC ACA CTG CAG CTC CGG CTT TTC CTC TAC CAG GGG
    ACC CGA GGG GAC TCG CGG TCG ACG GGG TCG GAC CGT CCG GAC CTG GAC GAC CTG TGT GAC GTC GAG GCC GAA AAG GAG ATG GTC CCC
    W   A   P   L   S   A   S   C   P   S   L   A   G   C   L   D   T   L   Q   L   R   L   F   L   Y   Q   G
        88                              90                                          100                                     110                             117
362 CTC CTG CAG GCC CTG GAA GGG ATC TCC CCC GAG TTG GGT ACC CTG GAC GTC CAG CTG GAC GTC TTT GCC ACC ATC
    GAG GAC GTC CGG GAC CTT CCC TAG AGG GGG CTC AAC CCA TGG GAC CTG CAG GTC GAC CTG CAG AAA CGG TGG TAG
    L   L   Q   A   L   E   G   I   S   P   E   L   G   T   L   D   V   Q   L   D   V   F   A   T   I
        118                                 120                                         130                                     140                                     147
452 TGG CAG CAG ATG GAA GAA CTG CTT GAC GTT CTA CGC CAC CTT GCC TCT GCT TTC CAG CCC CGG
    ACC GTC GTC TAC CTT CTT GAC GAA CTG CAA GAT GCG GTG GAA CGG AGA CGA AAG GTC GGG GCC
    W   Q   Q   M   E   E   L   L   D   V   L   R   H   L   A   S   A   F   Q   R   R
        148                                 150                                     160                                 170
542 GCA GGA GGG GTC CTA GTT CAA GAT CAG CGG GTA GAC CGG GTG TCG TAC AGC TTC CTG GAG GTC TCG TAC ATG CGG CAC CTT GCC CAC CGG GTG CTC CGC CAC CTG GCG CAG CCC TGA GGATCCA//
    CGT CCT CCC CAG GAT CAA GTT CTA GTC GCC CAT CTG GCC CAC AGC ATG TCG AAG GAC CTC CAG AGC ATG TAC GCC GTG GAA CGG GTG GCC CAC GAG GCG GTG GAC CGC GTC GGG ACT CCTAGGT
    A   G   G   V   L   V   Q   D   Q   R   V   D   R   V   S   Y   S   F   L   E   V   S   Y   M   R   H   L   A   H   R   V   L   R   H   L   A   Q   P
```

1. Wild Type human Granulocyte Colony Stimulating Factor
2. G51N Isoform
3. G51N/G94N Isoform
4. G94N Isoform
5. G51N/T133NG135S Isoform
6. T133NG135S Isoform
7. Molecular marker

GLYCOSYLATED HUMAN GRANULOCYTE COLONY-STIMULATING FACTOR (G-CSF) ISOFORM

CROSS-REFERENCE TO RELATED APPLICATIONS

Pursuant to 35 U.S.C. § 119, this application claims the benefit of Korean Patent Application No. 10-2002-0052364, entitled, GLYCOSYLATED HUMAN GRANULOCYTE COLONY-STIMULATING FACTOR (G-CSF) ISOFORM, filed Aug. 29, 2002, and named Eun Jung Lee, Hyun Seok Kim, Jong Sang Chung, Ki Wan Kim, Yeon Hyang Kim, Hyune Soo Lee, Hyung Kon Koh and Myung Suk Oh as inventors, which is hereby incorporated by reference for all purposes.

TECHNICAL FIELD OF THE INVENTION

The present invention, in general, relates to isoforms of human granulocyte colony-stimulating factor (G-CSF). More particularly, the present invention relates to human G-CSF isoforms having a modified amino acid sequence containing a glycosylation sequence Asn-X-Ser/Thr (N-X-S/T) at one or more specific amino acid positions according to the present invention, thus improving in vivo stability of human G-CSF, and their glycosylated forms.

BACKGROUND OF THE INVENTION

Colony-stimulating factors (CSFS) are cytokines that regulate the proliferation and differentiation of hematopoietic progenitor cells and the function of mature blood cells. Among CFSs, human granulocyte colony-stimulating factor (G-CSF) is thought to be a major stimulator of production of human neutrophilic granulocytes.

G-CSF is a glycoprotein produced in mononuclear cells, fibroblasts and endothelial cells. Purified G-CSF stimulates neutrophilic granulocyte colony formation from bone marrow progenitor cells, induces terminal differentiation (Nicola et al., JBC, Vol. 258, No. 14:9017-23, 1983), and suppresses self-replication and proliferation of leukocytes (Metcalf and Nicola, Leukemia Research, Vol. 9, 1:35-50, 1985). Human G-CSF (hG-CSF) was first purified from the human squamous carcinoma cell line CHU-2 (Nomura et al., EMBO J., Vol. 5, No. 5:871-76, 1986) and then from the human bladder carcinoma cell line 5637 (Welte et al., Proc. Narl. Acad. Sci. U.S.A., 82:1526-30, 1985; and Strife et al., Blood, Vol. 69, No. 5:1508-1523, 1987), in which the cell lines activity to promote human granulocyte colony formation was detected. The purified hG-CSF was identified to have a molecular weight of 18,000-19,000 Da and a pI value of 6.1 (the pI value varies from 5.5 to 6.1 according to the degree of glycosylation (Nomura et al., EMBO J., Vol.5, No. 5:871-76, 1986).

Neutrophilic granulocytes produced by stimulation of G-CSF are 10-20 μm in diameter, occupy over 70% of leukocytes, and play an important role in the protection of mammals from bacterial infection. However, owing to its half-life being shorter than macrophages and mononuclear cells, neutrophilic granulocytes must be produced continuously from pluripotent stem cells in bone marrow.

The hG-CSF isolated from human bladder carcinoma 5637 cells initially called pluripotent colony-stimulating factor or GM-CSF, based on the finding that it stimulates production of erythrocytes, megakaryocytes and macrophages in addition to neutrophilic granulocytes (Welte et al., Proc. Narl. Acad. Sci. U.S.A., 82:1526-30, 1985; Platzer et al., J. Exp Med, 162:1788-1801, 1985; and Nicola et al., Nature, 314:625-28, 1985), and affects pluripotent progenitor cells, for example, inducing proliferation of the human myeloid leukemia cell line HL-60 and the murine myelomonocytic leukemia cell line WEHI-3B(D+). However, in the studies excluding bone marrow cells and lymphocytes, the isolated protein was found to strongly stimulate neutrophilic granulocyte colony formation, and thus was assigned the nomenclature G-CSF (Welte et al., Proc. Narl. Acad. Sci. U.S.A., 82:1526-30, 1985; Metcalf, Science, 229:16-22, 1985; Metcalf, Blood, Vol. 67, No. 2:257-67, 1986; Metcalf, Proc. R. Soc. Lond. B., 230:389-423, 1987; and Sachs, Science, 238:1374-79, 1987). When treating with the isolated hG-CSF a mixture of hematopoietic colony-forming progenitor cells derived from human bone marrow cells lacking adherent cells and T-lymphocytes, neutrophilic granulocyte colony formation was observed after 7 days (Welte et al., Proc. Narl. Acad. Sci. U.S.A., 82:1526-30, 1985; and Platzer et al., J., Exp. Med., 162:1788-1801, 1985). In addition, the isolated hG-CSF stimulates differentiation of WEHI-3B(D+) cells.

Murine G-CSF (mG-CSF) has biological activity similar to hG-CSF. That is, mG-CSF produces neutrophilic granulocyte colonies in the CFU-GM assay, and induces terminal differentiation of WEHI-3B(D+) cells. In addition, hG-CSF functions not only in human bone marrow cells but also in murine bone marrow cells. Conversely, mG-CSF acts on both human and murine bone marrow cells.

In animals administered with G-CSF, the in vivo effects of G-CSF are regulated by its administered amount, and, when G-CSF treatment is stopped, the blood level of neutrophilic granulocytes is maintained at normal levels. However, the blood levels of G-CSF receptor-lacking blood cells, that is, erythrocytes, mononuclear cells and lymphocytes, are not changed.

In bone marrow cells and splenocytes, the G-CSF receptor is essential for differentiation of myeloid precursor cells into neutrophilic granulocytes. Also, the fact that mature neutrophilic granulocytes carry the G-CSF receptor suggests that G-CSF activates the mature cells. Receptor numbers are between 50 and 500 per cell. The concentration of G-CSF required for half-maximal stimulation is about 10 pM, while G-CSF has an equilibrium dissociation constant (Kd) of about 60-80 pM for G-CSF receptor binding. This fact indicates that the proliferation induced by G-CSF occurs in the presence of low levels of G-CSF receptors.

In addition to mature neutrophils, G-CSF affects neutrophil progenitor cells. That is, G-CSF enhances survival of mature neutrophils (Begley et al., Blood, Vol. 68, No. 1:162-66, 1986), and does not induce differentiation of the acute myeloblastic leukemia cells into mature cells, resulting in specific activation of neutrophils (Lopex et al., J. Immunol. Vol 131 No6:2983-2988, 1983; and Platzer et al., J. Exp. Med., 162:1788-1801, 1985).

In addition, when G-CSF was administered to an animal in which neutropenia had been induced by treatment with 5-fluorouracil and cyclophosphamide, proliferation of neutrophils was found to remarkably increase. In the clinical trials based on this finding, when G-CSF was administered into chemotheraphy-receiving malignant tumor patients (Bronchud et al., Br. J. Cancer, 56:809-13, 1987; Gabrilove et al., New England J. Med., Vol. 318, No. 22:1414-22, 1988; and Morstyn et al., Lancet, March 26:667-71, 1988), and patients undergoing bone marrow cell transplantation after treatment with radioisotopes of cyclophosphamide (Kodo et al., Lancet, July 2:38-39, 1988), patients feel only slight pain and G-CSF rarely causes side effects and induces an increase of neutrophilic granulocytes in both cases. These results indicate that G-CSF administration helps chemo-theraphy-received of bone marrow-transplanted patients, protecting them from bacterial or fungal infection occurring when recovery of the neutrophilic granulocyte levels to the normal levels is delayed. Such successful clinical trials allow G-CSF to be applied to a variety of patients suffering from neutropeina.

Molecular and genetic properties of G-CSF were identified by recombinant DNA technology (Clark and Kamen, Science, 236:1229-37, 1987), and a variety of studies of the functions of G-CSF were performed in vivo and in vitro using recombinant G-CSF. Human G-CSF was cloned from a cDNA library constructed with mRNA prepared from CHU-2 cells and human bladder carcinoma 5637 cells (Nagata et al., Nature, 319:415-18, 1986; Nagata et al., EMBO J., Vol. 5, No. 3:575-81, 1986; and Souza et al., Science, 232:61-65, 1986). In this study, two different cDNAs for human G-CSF were isolated. The nucleotide sequence analysis of both cDNAs indicated that they encode polypepetides consisting of 207 and 204 amino acids, respectively, and their translated products have a presequence (a secretory leader sequence) of 30 amino acids at the N-terminus. Two polypeptides coded by these cDNAs are different at the 35th position where three amino acids (Val-Ser-Glu) are deleted/inserted. Therefore, mature G-CSF protein is composed of 174 amino acids (MW 18,671 Da) or 177 amino acids (MW 18,987 Da).

The 174 amino acid G-CSF has an over 20-fold higher activity than the other consisting of 177 amino acids. However, it is not still clear that the two different forms are expressed in the human body. Human G-CSF does not have the N-glycosylation sequence (Asn-X-Ser/Thr (N-X-S/T)), but has an O-glycosylation site at the Thr-133 position. When recombinant human G-CSF prepared using the cDNA for human G-CSF was produced in E. coli (Souza et al., Science, 232: 61-65, 1986; Delvin et al., Gene, 65: 13-22, 1988) and animal cells (Tsuchiya et al., EMBO J., Vol. 6, No. 3: 611-16, 1987), recombinant human G-CSF produced in E. coli was found to have an activity identical to the natural form and the form expressed in animal cells. These results indicate that glycosylation is not critical essential for G-CSF activity. Human G-CSF ha no amino acid sequence homology with GM-CSF, interleukin-3 and M-CSF, and possesses two disulfide bonds (Cys36-Cys42 and Cys64-Cys74) formed by 4 of 5 cystein residues.

Due to their low in vivo stability, most of the physiologically active proteins used as drugs are excessively or frequently administered to patients in order to maintain an appropriate concentration capable of offering satisfactory therapeutic effects. This administration pattern causes pain in patients and inconvenience. Therefore, there is a need for development of physiologically active proteins having improved in vivo stability and thus resolving the problems in the prior art.

In order to improve in vivo stability of physiologically active proteins, interferon-alpha can be conjugated with polyethylene glycol as disclosed in International Pat. Publication No. WO9848840, and human growth hormone can be microcapsulated as disclosed in U.S. Pat. No. 6,399,103. However, these methods are disadvantageous in that additional steps should be carried out after production in a microorganism and purification of a target protein. In addition, cross-linkage can be formed at undesired positions. Moreover, the manufacturing processes do not ensure homogeneity of final products.

Another approach uses glycosylation. Cell surface proteins and secretory proteins produced in eukaryotic cells are modified by glycosylation. Glycosyl modification is know addition to their physiological properties.

SUMMARY OF THE INVENTION

Therefore, the present invention aims to prepare human G-CSF having improved in vivo stability and capable of being easily produced by producing human G-CSF at a glycosylated state in a cell line using the recombinant DNA technology.

In an aspect of the present invention, there is provided a human G-CSF isoform having a modified amino acid sequence containing a glycosylation sequence Asn-X-Ser/Thr (N-X-S/T) at one or more amino acid positions as described below:
T1-P10 (T1-P-L-G-P-A-S-S-L-P10) (SEQ ID NO: 13);
Y39-L71 (Y39-K-L-C-H-P-E-E-L-V-L-L-G-H-S-L-G-I-P-W-A-P-L-S-S-C-P-S-Q-A-L-Q-L71) (SEQ ID NO: 14);
L92-L99 (L92-E-G-I-S-P-E-L99) (SEQ ID NO: 15); and
G125-S142 (G125-M-A-P-A-L-Q-P-T-Q-G-A-M-P-A-F-A-S142) (SEQ ID NO: 16).

In another aspect of the present invention, there is provided a gene encoding a human G-CSF isoform having a modified amino acid sequence containing a glycosylation sequence Asn-X-Ser/Thr (N-X-S/T) at one or more amino acid positions as described above.

In a further aspect of the present invention, there is provided an expression vector carrying a gene encoding a human G-CSF isoform having a modified amino acid sequence containing a glycosylation sequence Asn-X-Ser/Thr (N-X-S/T) at one or more amino acid positions as described above.

In a still further aspect of the present invention, there is provided a host cell transformed or transfected with an expression vector carrying a gene encoding a human G-CSF isoform having a modified amino acid sequence containing a glycosylation sequence Asn-X-Ser/Thr (N-X-S/T) at one or more amino acid positions as described above.

In a still further aspect of the present invention, there is provided a method of preparing a glycosylated human G-CSF isoform, comprising the steps of culturing a eukaryotic host cell transformed or transfected with an expression vector carrying a gene encoding a human G-CSF isoform having a modified amino acid sequence containing a glycosylation sequence Asn-X-Ser/Thr (N-X-S/T) at one or more amino acid positions as described above; and isolating a glycosylated human G-CSF isoform from the culture supernatant or cell lysates.

In a still further aspect of the present invention, there is provided a glycosylated human G-CSF isoform prepared by glycosylation of a human G-CSF isoform having a modified amino acid sequence containing a glycosylation sequence Asn-X-Ser/Thr (N-X-S/T) at one or more amino acid positions as described above.

In a still further aspect of the present invention, there is provided a pharmaceutical composition comprising a glycosylated human G-CSF isoform prepared by glycosylation of a human G-CSF isoform having a modified amino acid sequence containing a glycosylation sequence Asn-X-Ser/Thr (N-X-S/T) at one or more amino acid positions as described above, and a pharmaceutically acceptable carrier.

In a still further aspect of the present invention, there are provided synthetic oligodeoxynucleotides used as primers in PCR for production of glycosylation sites in human G-CSF.

BRIEF DESCRIPTION OF THE DRAWINGS

The above and other objects, features and other advantages of the present invention will be more clearly understood from the following detailed description taken in conjunction with the accompanying drawings, in which:

FIG. 1 shows the nucleotide sequence (SEQ ID NO: 18 and 19 amino acid sequence (SEQ ID NO. 20) of natural human G-CSF, wherein arrows or straight lines above the nucleotide sequence indicate helix structure-containing regions in the tertiary structure of human G-CSF protein, the direction of the arrows represents the orientation of the helix along the amino acid sequence, and natural mature human G-CSF possesses a O-linked glycosylation site, functional in human or eukaryotic cells, at the 133rd Threonine residue;

DETAILED DESCRIPTION OF THE INVENTION

Figure 2:
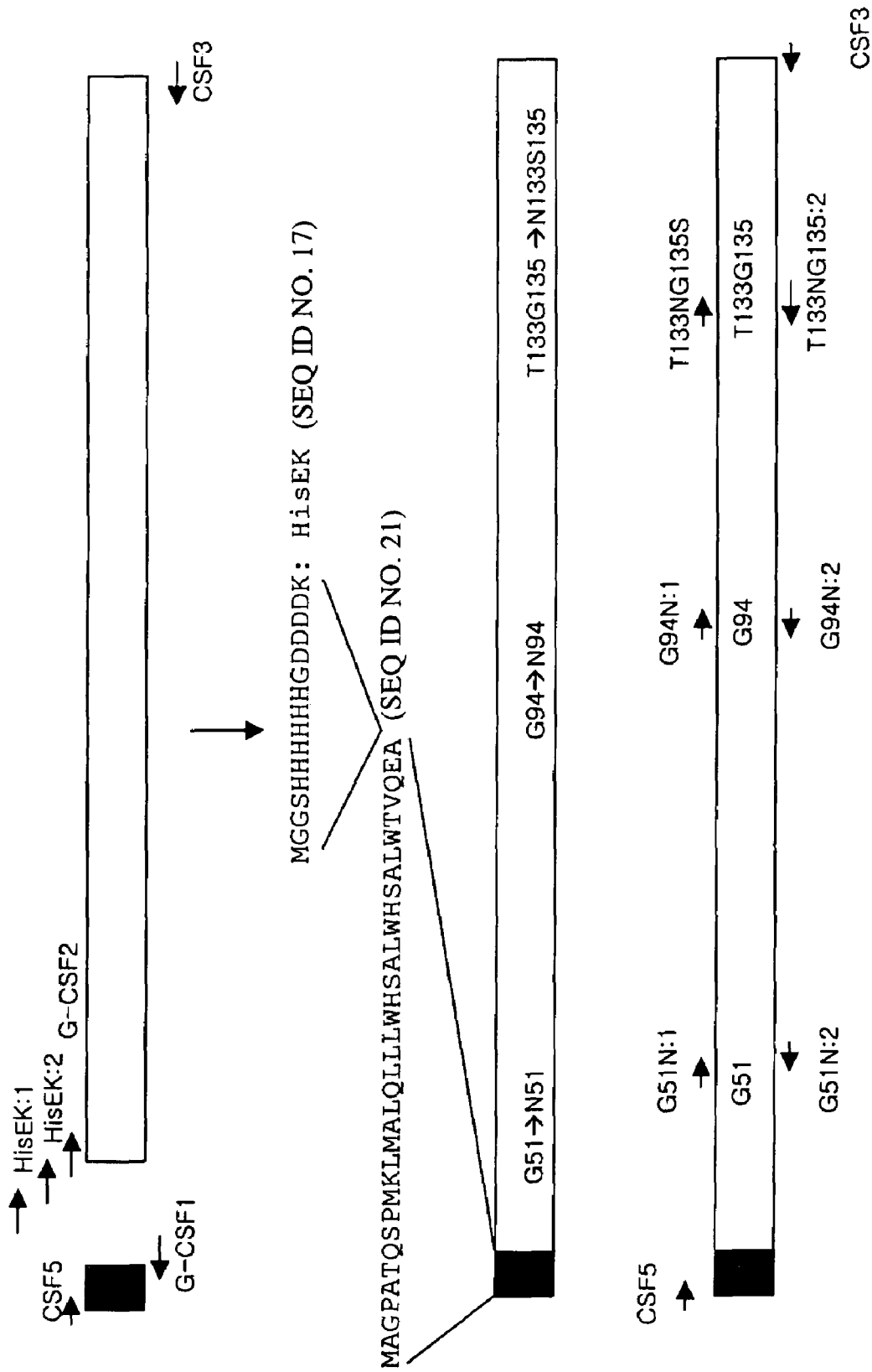
FIG. 2 shows modified amino acid positions of human G-CSF protein according to the present invention, wherein a pre-sequence is located at the N-terminus.

Best Modes for Carrying Out the Invention

The term "isoform of human granulocyte colony-stimulating factor (G-CSF)", as used herein, refers to an analogue or mutant having one or more amino acid modifications at one or more amino acid positions of a natural human G-CSF protein while maintaining innate biological activities.

Single capital letters representing amino acids, as used herein, represent the following amino acids according to the standard abbreviations defined by the International Union of Biochemistry:

A: Alanine; B: Asparagine or Aspartatic acid; C: Cysteine; D: Aspartic acid; E: Glutamic acid; F: Phenylalanine; G: Glycine; H: Histidine; I: Isoleucine; K: Lysine; L: Leucine;
M: Methionine; N: Asparagine; P: Proline; Q: Glutamine; R: Arginine; S: Serine; T: Threonine; V: Valine;
W: Tryptophan; Y: Tyrosine; and Z: Glutamine or Glutamic acid.

The designation "(one capital for an amino acid) (amino acid position) (one capital for another amino acid)", as used herein, means that the former amino acid is substituted with the latter amino acid at the designated amino acid position of human G-CSF. For example, G51N indicates that the glycine residue at the 51st position of a natural human G-CSF is substituted with asparagine.

Primers used for introduction of a glycosylation motif in the present invention are designated as "(one capital for an amino acid) (amino acid position) (one capital for another amino acid) 1 or 2", wherein 1 means a primer complementary to a 5' to 3'-orientated single-stranded template of a double-stranded nucleotide and 2 means a primer complementary to a 3' to 5'-orientated single-stranded template of the double-stranded nucleotide.

Secretory proteins produced in eukaryotic host cells are modified by addition of one or more oligosaccharide moieties. This modification, called glycosylation, is known to significantly affect physiological properties of proteins, and to be critical for stability, secretion and intracellular location of proteins. Proper glycosylation may be essential for biological activity of some proteins.

In fact, when a gene derived from eukaryotic cells is expressed in bacteria lacking an intracellular process responsible for protein glycosylation, the unglycosylated translational product generally has reduced activity.

Glycosylation occurs at specific positions along the backbone of a polypeptide. There are two types of glycosylation. O-linked glycosylation links an oligosaccharide chain to the hydroxy group (—OH) of a serine and/or threonine residue in the protein. N-linked glycosylation begins with the linkage of an oligosaccharide chain to the amide group (—NH) of asparagine residue. In particular, N-type glycosylation occurs in the specific amino acid sequence, Asn-X-Ser/Thr (N-X-S/T) (X is any amino acid excluding proline). N-linked oligosaccharide has a structure distinct from O-linked oligosaccharide, and glycosylated residues found in the N-linked type also differ from the O-linked type. For example, in O-linked oligosaccharides, N-acetylgalactosamine always attaches to serine or threonine, while, in N-linked oligosaccharides, N-acetylglucosamine is linked to asparagine. Also, the O-linked oligosaccharide typically contains 4 or less sugar residues. In contrast, the N-linked oligosaccharides comprise 5 or more sugar residues, essentially including N-acetylglucosamine and mannose.

The present invention relates to a human G-CSF isoform having a modified amino acid sequence containing a glycosylation sequence Asn-X-Ser/Thr (N-X-S/T) at one or more specific amino acid positions according to the present invention, thus improving in vivo stability of a natural human G-CSF protein. In the present invention, glycosylation of human G-CSF was identified to be induced by glycosylation sequence insertion at any amino acid position, except for positions within helix structure-forming regions.

In an aspect, the present invention includes a human G-CSF isoform having a modified amino acid sequence containing a glycosylation sequence Asn-X-Ser/Thr (N-X-S/T) at one or more amino acid positions as described below:

T1-P10 (T1-P-L-G-P-A-S-S-L-P10) (SEQ ID NO: 13);
Y39-L71 (Y39-K-L-C-H-P-E-E-L-V-L-L-G-H-S-L-G-I-P-W-A-P-L-S-S-C-P-S-Q-A-L-Q-L71) (SEQ ID NO: 14);
L92-L99 (L92-E-G-I-S-P-E-L99) (SEQ ID NO: 15); and
G125-S142 (G125-M-A-P-A-L-Q-P-T-Q-G-A-M-P-A-F-A-S142) (SEQ ID NO: 16).

In a preferred aspect, the invention includes a human G-CSF isoform having a modified amino acid sequence containing a glycosylation sequence Asn-X-Ser/Thr (N-X-S/T) at one or more amino acid positions as described below:

Y39-L71 (Y39-K-L-C-H-P-E-E-L-V-L-L-G-H-S-L-G-I-P-W-A-P-L-S-S-C-P-S-Q-A-L-Q-L71) (SEQ ID NO: 14);
L92-L99 (L92-E-G-I-S-P-E-L99) (SEQ ID NO: 15); and
G125-S142 (G125-M-A-P-A-L-Q-P-T-Q-G-A-M-P-A-F-A-S142) (SEQ ID NO: 16).

In a preferred aspect, the invention includes a human G-CSF isoform having a modified amino acid sequence containing a glycosylation sequence Asn-X-Ser/Thr (N-X-S/T) at one or more amino acid positions as described below:
Y39-L71 (Y39-K-L-C-H-P-E-E-L-V-L-L-G-H-S-L-G-I-P-W-A-P-L-S-S-C-P-S-Q-A-L-Q-L71) (SEQ ID NO: 14);
L92-L99 (L92-E-G-I-S-P-E-L99) (SEQ ID NO: 15); and
G125-S142 (G125-M-A-P-A-L-Q-P-T-Q-G-A-M-P-A-F-A-S142) (SEQ ID NO: 16).

In a more preferred aspect, the invention includes a human G-CSF isoform having a modification of Glycine-51 to asparagine, of Glycine-94 to asparagine, or of Threonine-133 and Glycine-135 to asparagine and serine, respectively, or having all of the aforemenetioned modifications.

In the present invention, in order to achieve additional glycosylation of human G-CSF, a DNA sequence encoding human G-CSF is modified at one or more nucleotides, and the mutated DNA is introduced into a eukaryotic cell capable of carrying out protein glycosylation and expression therein. Therefore, additional glycosylation of human G-CSF is achieved by modifying its corresponding DNA sequence in order to introduce the Asn-X-Ser/Thr (N-X-S/T) sequence thereinto.

In an aspect, the present invention includes a gene encoding a human G-CSF isoform having a modified amino acid sequence containing a glycosylation sequence Asn-X-Ser/Thr (N-X-S/T) at one or more amino acid positions as described below:
T1-P10 (T1-P-L-G-P-A-S-S-L-P10) (SEQ ID NO: 13);
Y39-L71 (Y39-K-L-C-H-P-E-E-L-V-L-L-G-H-S-L-G-I-P-W-A-P-L-S-S-C-P-S-Q-A-L-Q-L71) (SEQ ID NO: 14);
L92-L99 (L92-E-G-I-S-P-E-L99) (SEQ ID NO: 15); and
G125-S142 (G125-M-A-P-A-L-Q-P-T-Q-G-A-M-P-A-F-A-S142) (SEQ ID NO: 16).

In a preferred aspect, the present invention includes a gene encoding a human G-CSF isoform having a modified amino acid sequence containing a glycosylation sequence Asn-X-Ser/Thr (N-X-S/T) at one or more amino acid positions as described below:
Y39-L71 (Y39-K-L-C-H-P-E-E-L-V-L-L-G-H-S-L-G-I-P-W-A-P-L-S-S-C-P-S-Q-A-L-Q-L71) (SEQ ID NO: 14);
L92-L99 (L92-E-G-I-S-P-E-L99) (SEQ ID NO: 15); and
G125-S142 (G125-M-A-P-A-L-Q-P-T-Q-G-A-M-P-A-F-A-S142) (SEQ ID NO: 16).

In a preferred aspect, the present invention includes a gene encoding a human G-CSF isoform having a modification of Glycine-51 to asparagine, of Glycine-94 to asparagine, or of Threonine-133 and Glycine-135 to asparagine and serine, respectively, or having all of the aforemenetioned modifications.

In an aspect of the present invention, a gene encoding human G-CSF is obtained from a eukaryotic cell expressing human G-CSF. The gene may be cloned and isolated by the methods known in the art.

The human G-CSF gene obtained according to the aforementioned method may be modified at one or more selected codons. The term "modification", as used herein, refers to substitution of one or more codons in a human G-CSF-encoding gene with a different codon and thus to cause change of an amino acid sequence of human G-CSF. In more detail, the term "modification" means that one or more amino acid residues of human G-CSF are substituted with a different amino acid residues of order to introduce a glycosylation sequence Asn-X-Ser/Thr (N-X-S/T) into an amino acid sequence of human G-CSF and thus allow additional N-linked glycosylation. For example, in Example 3, when the 51st glycine residue is substituted with asparagine, since the 53rd residue is serine, a glycosylation sequence Asn-X-Ser/Thr (N-X-S/T) is formed, thus allowing additional N-linked glycosylation of human G-CSF. In addition, when the 94th glycine residue is substituted with asparagine, since the 96th amino acid residue is serine, an Asn-X-Ser/Thr (N-X-S/T) sequence is formed, thus allowing additional N-linked glycosylation of human G-CSF. Further, when the 133rd threonine and 135th glycine residues are substituted with asparagine and serine, respectively, an Asn-X-Ser/Thr (N-X-S/T) sequence is formed, thus allowing additional N-linked glycosylation of human G-CSF.

In an aspect of the present invention, oligonucleotides containing codons encoding desired amino acid modifications used in the present invention are composed of about 25 nucleotides. Shorter oligonucleotides can be employed, but optimal oligonucleotides, at both left and right regions of modified codons, contain 12 to 15 nucleotides complementary to a template. These oligonucleotides can effectively hybridize with a template DNA. Oligonucleotides used for production of additional glycosylation sites in the present invention are listed in Table 1 in Example 3. These oligonucleotides may be synthesized by the techniques known in the art.

In an aspect of the present invention, there is provided a DNA sequence encoding a human G-CSF isoform having a modified amino acid sequence. PCR is carried out using human G-CSF cDNA as a template and modification-encoding oligonucleotides as primers. Primers hybridize with their complementary single-stranded DNA produced by denaturation of a double-stranded DNA template during heating. DNA polymerase adds nucleotides to the 3'—OH of the modification-encoded primer one by one in a complementary manner to a template in the 5' to 3' direction. The newly synthesized strand contains the modification-encoded primer, thus giving a gene encoding a desired modification. The newly synthesized strand is used as a template DNA in the extension step of PCR, resulting in amplification of a gene encoding the modification. For example, in Example 3, in order to change the 51st glycine residue to asparagine, PCR was carried out using natural G-CSF DNA as a template with a primer set consisting of CSF5 and G51N2, or G51N1 and CSF3. As a result, two DNA fragments were obtained, which carry a codon encoding asparagine at the 51st glycine residue. Using the two DNA fragments as templates, a second PCR was carried out with a primer set of CSF5 and CSF3, thus giving a modified gene encoding G-CSF-G51N capable of being additionally glycosylated by modification of the 51st amino acid residue with asparagine.

In an additional aspect of the present invention, there is provided a human G-CSF isoform carrying two or more amino acid modifications. A mutant harboring two or more amino acid modifications may be prepared by a variety of methods. In case that two or more amino acids to be modified are spaced close to each other on a polypeptide, all desired modifications are encoded in one oligonucleotide and thus simultaneously achieved. Therefore, a mutated human G-CSF protein having two or more amino acid modifications may be prepared by the same method as in preparing the mutated human G-CSF gene carrying one nucleotide modification, excepting for use of oligonucleotides containing two or more amino acid modifications as primers. However, in case that two or more amino acids to be modified are spaced far apart (in case that over 10 amino acids are present between two amino acids to be modified), all desired modifications can not be encoded in one oligonucleotide.

Instead, different methods should be used. One method is to prepare individual oligonucleotides for each amino acid modification. When the oligonucleotides are annealed simultaneously to a single-stranded template DNA, a newly synthesized secondary single-stranded DNA encodes all of the desired amino acid modifications. Another approach used in the present invention to produce such a human G-CSF isoform includes two mutagenesis experiments. In the primary mutagenesis, using natural DNA as a template, one oligonucleotide containing one desired amino acid modification is annealed to the template, and thus heteroduplex DNA is produced. In the secondary mutagenesis, the heteroduplex DNA is used as a template. The template already carries at least one modification. When one oligonucleotide having an additional amino acid modification is annealed to the template, the resulting DNA encodes both of the modifications, and can be used as a template at the third mutagenesis. That is, the method of modifying two or more nucleotides is to repeat several times the method of modifying one nucleotide. For example, in Example 3, in order to modify both the 51st glycine to asparagine and the 94th glycine to asparagine in natural human G-CSF, the 94th amino acid was modified first, and, using the resulting DNA as a template, the 51st amino acid was modified. As a result, a mutated human G-CSF gene having both of the modifications was produced.

The DNA sequence encoding a human G-CSF isoform according to the present invention can be synthesized by the standard methods known in the art, for example, using an automatic DNA synthesizer (Biosearch, Applied Biosystem™).

The glycosylated human G-CSF isoform according to the present invention is typically prepared by (a) inserting a DNA sequence encoding the human G-CSF isoform into a vector carrying one or more expression control sequences while the DNA sequence is operatively linked to and thus under control of the expression control sequence; (b) transforming or transfectant a host cell with the resulting recombinant expression vector; and (c) culturing the transformant or transfectant in a proper medium and under conditions suitable for the expression of the human G-CSF isoform DNA sequence, and isolating a glycosylated human G-CSF isoform.

With respect to this, the present invention provided a host cell transformed or tranfected with such a recombinant expression vector carrying a DNA sequence encoding a human G-CSF isoform.

It should of course be understood that all vectors and expression control sequences do not function equally to express the nucleotide sequence of the present invention. Similarly, all kinds of host cells do not function equally in the same expression system. However, those of ordinary skill in the art can select suitable vectors, expression control sequences and host cells within a scope of the present invention without excessive experimental burden. For example, in selecting a vector, the host should be considered because the vector must replicate in it. Also, the vector's copy number, the ability to control the copy number, and the expression of any other proteins encoded by the vector, such as antibiotic markers, should be considered. In selecting an expression control sequence, a variety of factors should also be considered. These factors include the relative strength of the sequence, its controllability, and its compatibility with the nucleotide sequence of the present invention, particularly as regards potential secondary structures. In addition, hosts should be selected in consideration of their compatibility with the chosen vector, the toxicity of the product coded for by the nucleotide sequence, their secretion characteristics, their ability to fold the polypeptide correctly, their fermentation or culture requirements, and the ease of purification of the products coded for by the nucleotide sequence.

The term "vector", as used herein, means a DNA molecule serving as a vehicle capable of stably carrying exogeneous genes into host cells. For useful application, a vector should be replicapable, have a system for introducing itself into a host cell, and possess selectable markers. In addition, the term "recombinant expression vector", as used herein, refers to a circular DNA molecule carrying exogeneous genes operably linked thereto to be expressed in a host cell. When introduced into a host cell, the recombinant expression plasmid has the ability to replicate regardless of host chromosomal DNA, copy itself at a high copy number, and to produce heterogeneous DNA. As generally known in the art, in order to increase the expression level of a transfected gene in a host cell, the gene should be operably linked to transcription and translation regulatory sequences functional in a host cell selected as an expression system. Preferably, the expression regulation sequences and the exogenous genes may be carried in a single expression vector containing bacteria-selectable markers and a replication origin. In case that eukaryotic cells are used as an expression system, the expression vector should further comprise expression markers useful in the eukaryotic host cells.

In order to express the DNA sequence encoding the human G-CSF isoform according to the present invention, various expression vectors may be employed. Preferably, since the human G-CSF isoform should be glycosylated, expression vectors suitable for eukaryotic host cells should be used. Expression vectors useful for eukaryotic host cells contain expression control sequences derived from, for example, SV40, bovine papillomavirus, adenovirus and cytomegalovirus. In detail, examples of the vectors include pCDNA3.1(+)/Hyg (Invitrogen, Carlsbad, Calif., USA) and pCI-neo (Stratagen, La Jolla, Calif., USA). Expression vectors useful for yeasts include 2μ plasmid and its isoforms, POT1 vector (U.S. Pat. No. 4,931,373) and pPICZ A, B, or C (Invitrogen). Expression vectors useful for insect cells include pVL 941, pBluebac 4.5 and pMelbac (Invitrogen).

The term "expression control sequences" refers to nucleotide sequences necessary or advantageous for expression of the polypeptide of the present invention. Each control sequence may be native or foreign to the nucleotide sequence encoding the polypeptide. Non-limiting examples of the expression control sequences include leader sequences, polyadenylation sequences, propeptide sequences, promoters, enhancers or upstream activating sequences, signal peptide sequences, and transcription terminators. The expression control sequence contains at least one promoter sequence.

In order to express the nucleotide sequence of the present invention, any of various expression control sequences may be inserted into the expression vectors used in the present invention. Examples of expression control sequences suitable for directing protein expression in mammalian cells include SV40 and early and late promoters of adenovirus, MT-1 (metallothionein gene) promoter, human cytomegalovirus immediate-early gene promoter (CMV), Rous sarcoma virus (RSV) promoter, and human ubiquitin C (UbC) promoter. In addition, to improve expression level in mammalian cells, a synthetic intron may be inserted into the 5'-untranslated region of the nucleotide sequence encoding the polypeptide. Examples of expression control sequences suitable for directing protein expression in insect cells include polyhedrin promoter, P10 promoter, baculovirus 39K delayed-early gene promoter and SV40 polyadenylation sequence. Examples of expression control sequences suitable for directing protein expression in yeasts include the promoter of the yeast α-mating system, yeast triose-phosphate isomerase (TPI) promoter and ADH2-4c promoter. Examples of expression control sequences suitable for directing protein expression in fungal cells include ADH3 promoter and terminators.

Another useful component of vectors used in the present invention is signal peptide sequence. Signal peptide sequence is typically located at the 5' region of a gene encoding a protein, and thus translated at a linked state to the N-terminus of the protein. The presence or absence of a signal peptide will, for example, depend on the expression host cell used for the production of the polypeptide to be expressed (whether it is an intracellular or extracellular polypeptide) and whether it is desirable to obtain secretion. When a polypeptide is secreted from the cells in which it is expressed, the signal peptide is present at the polypeptide. Such a signal peptide, if present, should be recognized by the cell selected for the expression of the polypeptide. The signal peptide may be homologous (normally associated with a desired polypeptide) or heterologous (derived from a different polypeptide) to the polypeptide, and may be homologous or heterologous to the host cells.

When a nucleotide sequence is arranged with another nucleotide sequence in a functional relationship, this arrangement is defined as "operably linked". The nucleotide sequences may be a gene and control sequences, which are linked in a manner that gene expression is induced when a suitable molecule (for example, transcription-activating protein) binds to the control sequence(s). For example, when a pre-sequence or secretory leader facilitates secretion of a mature protein, it is referred to as "operably linked to the protein". A promoter is operably linked with a coding sequence when it regulates transcription of the coding sequence. A ribosome-binding site is operably linked to a coding sequence when it is present at a position allowing translation of the coding sequence. Typically, the term "operably linked" means that linked nucleotide sequences are in contact with each other.

In case of a secretory leader sequence, the term means that it contacts a coding sequence and is present within a leading frame of the coding sequence. However, an enhancer needs not necessarily contact with a coding sequence. Linkage of the nucleotide sequences may be achieved by ligation at convenient restriction enzyme recognition sites. In case of the absence of restriction enzyme recognition sites, oligonucleotide adaptors or linkers may be used, which are synthesized by the conventional methods.

A suitable vector, containing the aforementioned components (that is, expression control sequences) as well as a gene encoding the human G-CSF isoform, may be prepared by the conventional recombinant DNA technology. To form a desired vector, isolated DNA fragments are digested with suitable restriction enzymes and ligated in a unique order and orientation.

DNA molecules may be digested using specific restriction enzymes in a buffer solution. Typically, about 0.2-1 µg of plasmid DNA or a DNA fragment is digested with about 1-2 units of a restriction enzyme in 20 µl of a buffer solution. Suitable buffer, DNA concentration, and incubation time and temperature are specified by a company manufacturing restriction enzymes. Typically, proper incubation is carried out at 37° C. for about 1-2 hrs, but some restriction enzymes require higher temperatures. After incubation, enzymes and other impurities are removed by extraction with a mixture of phenol and chloroform, and DNA is recovered from the aqueous layer by precipitation with ethanol. Herein, in order to produce a functional vector, one end of a digested DNA fragment should be complementary to that of another digested DNA fragment.

The digested DNA fragments should be separated in size by electrophoresis and selected. DNA may be electrophoresed through agarose or a polyacrylamide matrix. The matrix may be determined depending on the size of the DNA fragments to be separated. After electrophoresis, DNA is extracted from the matrix by electroelution, or by simply melting agarose when low-melting point agarose is used.

DNA fragments to be ligated should be added to a reaction solution at an identical molar ratio. The reaction solution contains ATP, ligase buffer and 10 units of T4 ligase per 0.5 ug of DNA. To ligate a DNA fragment to a vector, the vector should be first linearized by digestion with suitable restriction enzymes. The linearized vector should be treated with alkaline phosphatase or calf intestine alkaline phosphatase. This alkaline phosphatase treatment prevents self-ligation of the linearized vector. Then, a host cell is transformed or transfected with the prepared recombinant expression vector.

Typically, host cells having high introduction efficiency of foreign DNA and having high expression levels of an introduced gene may be used. In particular, as a host cell, a eukaryotic cell should be used, which is capable of glycosylating the human G-CSF isoform of the present invention. Examples of suitable yeast host cells include strains of *Saccharomyces* and *Hansenula*. Examples of suitable fungal host cells include *Tricoderma, Fusarium* and *Aspergillus* species. Examples of suitable insect host cells include Lepidoptora cell lines such as Sf9 or Sf21. Examples of suitable mammalian host cells include CHO cell lines, COS cell lines such as COS1 or COS7, animal cell lines such as BHK cell line or mouse cells, and tissue-cultured plant cells and human cells.

Polynucleotide may be introduced into a host cell by the methods described in basic experimental guide books (for example, Davis et al., Basic Methods in Molecular Biology (1986); and Sambrook, J., et al. (1989) "Molecular Cloning" A Laboratory Manual 2nd edition). The preferred methods for introducing polynucleotide into a host cell include, for example, calcium phosphate transfection, DAEA-dextran mediated transfection, transvection, microinjection, cationic lipid-mediated transfection, electroporation, transduction, scrape loading, ballistic introduction, and infection.

In the production methods of the present invention, the host cells are cultivated in a nutrient medium suitable for production of the polypeptide using methods known in the art. For example, the cells may be cultivated by shake flask cultivation, small-scale or large-scale fermentation in laboratory or industrial fermenters performed in a suitable medium and under conditions allowing the polypeptide to be expressed and/or isolated. The cultivation takes place in a suitable nutrient medium containing carbon and nitrogen sources and inorganic salts, using procedures known in the art. Suitable media are well known to those of ordinary skill in the art, and are commercially available of may be prepared according to published compositions. If the polypeptide is secreted into the nutrient medium, the polypeptide can be recovered directly from the medium. If the polypeptide is not secreted, it can be recovered from cell lysates.

The produced polypeptide may be recovered by the methods known in the art. For example, the polypeptide may be recovered from the nutrient medium by conventional procedures including, but not limited to, centrifugation, filtration, extraction, spray drying, evaporation, or precipitation. The polypeptides may be purified by a variety of procedures known in the art including, but not limited to, chromatography (e.g., ion exchange, affinity, hydrophobic, chromatofocusing, and size exclusion), electrophoresis, differential solubility (e.g., ammonium sulfate precipitation), SDS-PAGE, or extraction).

The present invention provides glycosylated human G-CSF isoform having additional glycosylation obtained by the aforementioned process. In the present invention, the description "glycosylated human G-CSF isoform having additional glycosylation" may be defined as an expression product spontaneously glycosylated by introducing a human G-CSF gene modified to allow one or more insertions of a glycosylation sequence Asn-X-Ser/Thr (N-X-S/T) into a eukaryotic host cell and then expressing the gene in the host cell. That is, it refers to a heterogenous molecule formed by covalent bonding of sugar residues to the amide group (—NH) of the additional glycosylation site Asn-X-Ser/Thr (N-X-S/T) in the human G-CSF isoform.

In addition, the present invention provides a pharmaceutical composition comprising a glycosylated human G-CSF isoform having additional glycosylation and a pharmaceutically acceptable carrier. Therapeutic preparations of the glycosylated human G-CSF isoform for therapeutic administration may be prepared by mixing the glycosylated human G-CSF isoform having a desired purity with a physiologically acceptable carrier, exipient or stabilizer, and formulating the mixture into an aqueous formulation with lyophilized cake (Remington's Pharmaceutical Sciences, 16th edition, Olso, A., ED., (1980)). Pharmaceutical preparations for parenteral administration may be prepared by mixing the glycosylated human G-CSF isoform as described herein and a pharmaceutically acceptable carrier and formulating the mixture into an adminsterable form (solutions, suspensions or emulsions).

The pharmaceutically acceptable carrier, exipient or stabilizer should be nontoxic to the recipients at its dosage and concentration, and compatible with other components in the pharmaceutical composition. For example, the pharmaceutical composition should not contain oxidizing agents or other materials known to be harmful to the polypeptide.

Suitable carriers include phosphate, citric acid and other buffers such as organic acid; antioxidants including ascorbic acid; low molecular weight polypeptide; serum albumin, gelatin and proteins such as immunoglobulin; hydrophilic polymers such as polyvinylpyrrolidone; amino acids such as glycine, glutamine, arginine or lysine; monosaccharides, disaccharides and other polysaccharides, such as glucose, mannose or dextrin; chelating factors such as EDTA; metal ions such as zinc, cobalt or copper; glycoalcohols such as mannitol or sorbitol; salt-forming counter-ions such as sodium; and/or non-ionic surfactants such as Tween, pluronic or polyethylene glycol (PEG).

In case of being administered for treatment purposes, the glycosylated human G-CSF isoform should be sterilized. Sterilization may be achieved easily by filteration through a sterile filtration membrane.

The pharmaceutical composition of the glycosylated human G-CSF isoform should be typically stored in a container with a sterile access port, for example, a bag or vial for intravenous injection, which has a stopple penetrable by a needle for subcutaneous injection. The pharmaceutical composition of the present invention, which is aqueous or lyophilized, may be stored in a single-dose or multidose container, for example, sealed vials or ampules. To obtain the lyophilized form, 5 ml of a filterated 1% (w/v) human G-CSF isoform solution is put into a 10-ml vial, and then lyophilized. An injectable solution may be prepared by dissolving (reconstituting) the lyophilized human G-CSF isoform using bacteriostatic water for injection.

Including parenteral administration, the glycosylated human G-CSF isoform may be directly administered to animals by a suitable technique, and the administration may be performed locally or systematically. Specific administration routes may be determined, for example, depending on the medical history of a patient in whom side effects of human G-CSF are recognized or expected. Parenteral administrations include subcutaneous, intramuscular, intravenous, intraarterial and intraperitoneal injections. Most preferably, the administration may be achieved by continuous injection (e.g., minipump such as osmotic pressure pump) or injection using a syringe via intraveneous or subcutaneous route.

The glycosylated human G-CSF isoform of the present invention will be administered to patients in a "therapeutically effective" dose, i.e. a dose that is sufficient for obtaining the desired therapeutic effects in relation to the condition for which it is administered. The pharmaceutical composition of the glycosylated human G-CSF isoform should be prepared and administered consistently with preferred medical practices under consideration of specific states to be treated, clinical conditions of individual patients (especially, side effects occurring upon administration of human G-CSF alone), delivery position of the glycosylated human G-CSF isoform, administration methods, administration schedule, and other requirements known to those skilled in the art. The therapeutically effective dose of the glycosylated human G-CSF isoform may be determined taking such factors into consideration. Daily dosage of the human G-CSF isoform of the present invention is typically about 1 μg to 100 mg, and preferably, 0.01 mg to 1 mg.

The present invention will be explained in more detail with reference to the following examples in conjunction with the accompanying drawings. However, the following examples are provided only to illustrate the present invention, and the present invention is not limited to the examples.

EXAMPLE 1

Preparation of Human G-CSF Gene

Human G-CSF gene was obtained from a bacterial strain carrying human G-CSF gene capable of being expressed in animal cells, which has been held in our laboratory. Nucleotide sequence and amino acid sequence of human G-CSF are given FIG. 1.

EXAMPLE 2

Selection of Positions to be Modified in Human G-CSF

Using Boone's structure analysis results (J. Biol. Chem., vol. 5, 8770, (1992)), sites to be additionally glycosylated were selected in human G-CSF. Primarily, regions having a helix structure on the amino acid sequence of human G-CSF were excluded (FIG. 1). Then, taking into consideration the spatial position of Thr-133 as an O-linked glycosylation site in the tertiary structure of human G-CSF, regions easily modified into an N-linked glycoylation motif were selected.

enzyme NcoI. The coding sequence of mature human G-CSF was primarily amplified by PCR using a primer set of HisEK2 and CSF3, and then the amplified product was secondarily amplified using HisEK1 and CSF3 primers. The resulting PCR product was digested with NcoI, and ligated to the NcoI-digested pre-sequence using T4 DNA ligase. Thereafter, using the ligated product as a template, PCR was carried out with CSF5 and CSF3 primers. The amplified DNA product was digested with HindIII and BamHI, and inserted into pcDNA3.1-Hygro(+) vector digested with the same restriction enzymes using T4 DNA ligase, thus producing an expression vector.

TABLE 1

Synthetic oligodeoxynucleotides used as primers for production of additional glycosylation sites

| Primer names | Sequences of primers | SEQ ID NOs |
|---|---|---|
| HisEK: 1 | 5'-ATG GGG GGT TCT CAT CAT CAT CAT CAT CAT GGG-3' | 1 |
| HisEK: 2 | 5'-CAT CAT CAT CAT CAT GGG GAC GAT GAC GAT AAG-3' | 2 |
| CSF: 1 | 5'-ACC CCC CAT GGC TTC CTG CAC TGT CCA GTG-3' | 3 |
| CSF: 2 | 5'-GGG GAC GAT GAC GAT AAG ACC CCC CTG GGC CCT GCC-3' | 4 |
| G51N1 | 5'-GAG GAG CTG GTG CTG CTC AAC CAC TCT CTG GGC ATC CCC-3 | 5 |
| G51N2 | 5'-GGG GAT GCC CAG AGA GTG GTT GAG CAG CAC CAG CTC CTC-3' | 6 |
| G94N1 | 5'-CTC CTG CAG GCC CTG GAA AAC ATC TCC CCC GAG TTG GGT CCC-3' | 7 |
| G94N2 | 5'-GGG ACC CAA CTC GGG GGA GAT GTT TTC CAG GGC CTG CAG GAG-3' | 8 |
| T133NC135S: 1 | 5'-CCT GCC CTG CAG CCC AAC CAG AGC GCC ATG CCG GCC TTC-3' | 9 |
| T133NC135S: 2 | 5'-GAA GGC CGG CAT GGC GCT CTG GTT GGG CTG CAG GGC AGG-3' | 10 |
| CSF5 | 5'-TCC CAA GCT TAT GGC TGG ACC TGC CAC CCA G-3' | 11 |
| CSF3 | 5'-TGG GAT CCT CAG GGC TGG GCA AGG TGG CGT AG-3' | 12 |

EXAMPLE 3

Preparation of Human G-CSF Isoform

A gene encoding a modified human G-CSF protein having one or more amino acid modifications and thus carrying additional glycosylation sites was prepared by performing PCR using synthetic oligodeoxynucleotides as primers. The used synthetic oligodeoxynucleotides are listed in Table 1, below.

As shown in FIG. 2, in order to introduce additional glycosylation sites into human G-CSF, G51, G94, T133 and G135 were selected. The 51st glycine and 94th glycine residues were modified with asparagine, respectively. The 133rd threonine and 135th glycine residues were modified with asparagine and serine, respectively. The synthetic oligodeoxynucleotides used in these modifications are marked in FIG. 2. The direction of arrows represents the 5' to 3' orientation of each oligodeoxynucleotide.

To facilitate purification of the expressed human G-CSF protein, an additional amino acid sequence (HisEK) was inserted between the pre-sequence and the N-terminus of mature human G-CSF. The inserted amino acid sequence was M-G-G-S-H-H-H-H-H-H-G-D-D-D-D-K. (SEQ ID NO: 17). This insertion allows isolation of the expressed human G-CSF isoform protein by metal affinity chromatography. The isolated protein obtained by metal affinity chromatography was treated with enterokinase, and again subjected to metal affinity chromatography, thus giving a high-purity human G-CSF isoform protein.

Figure 3:
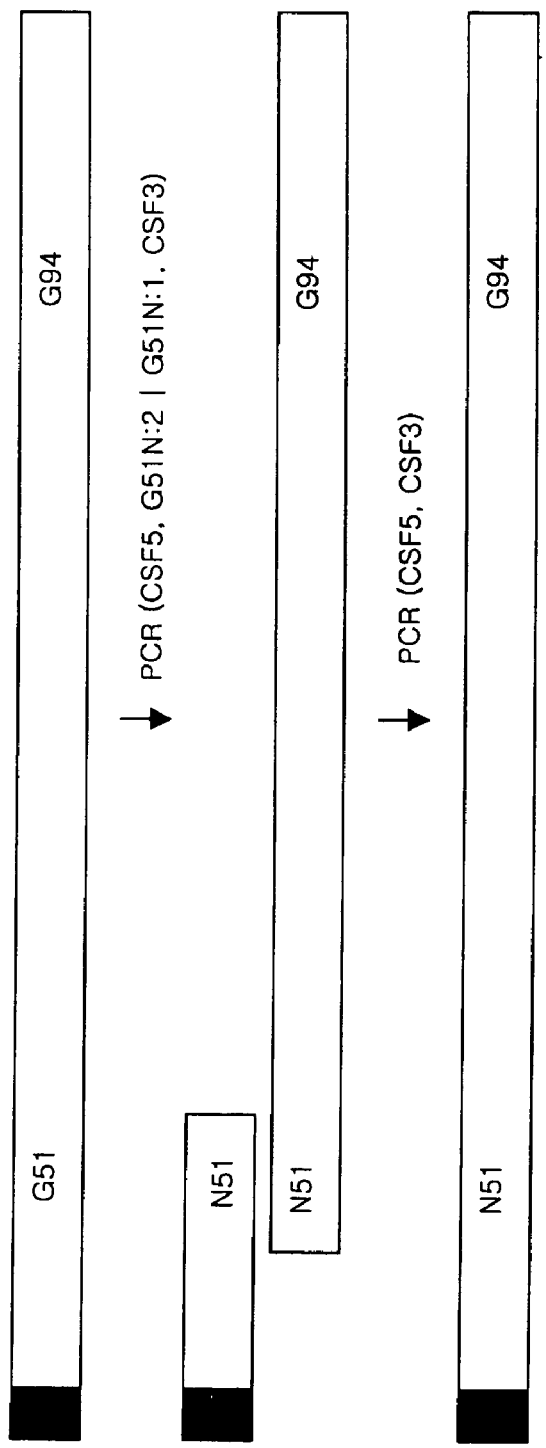
FIG. 3 shows a procedure for modifying the 51st glycine residue of natural human G-CSF with asparagine.

The HisEK sequence was introduced into human G-CSF as follows. The pre-sequence was amplified by PCR using a primer set of CSF5 and CSF1, and digested with a restriction (1) Preparation of Human G-CSF Isoform With G51N Modification (FIG. 3)

The human G-CSF gene prepared in Example 1 was amplified by PCR using a primer set of CSF5 and G51N2 and another primer set of G51N1 and CSF3. The resulting DNA fragments were purified, and denatured with 0.2 M NaOH/2 mM EDTA. Using the denatured DNA fragments as templates, PCR was carried out with a primer set of CSF5 and CSF3 in order to produce a mutated human G-CSF gene having a modification of the 51st glycine residue to asparagine. As a result, as shown in FIG. 3, two DNA fragments carrying a codon corresponding to asparagine instead of glycine at the 51st amino acid position were obtained. After the two DNA fragments were added into a PCR reaction mixture, secondary PCR was carried out using a primer set of CSF5 and CSF3, resulting in production of a modified G-CSF-G51N gene with a modification of the 51st amino acid position to asparagine, which can be additionally glycosylated.

Figure 4:
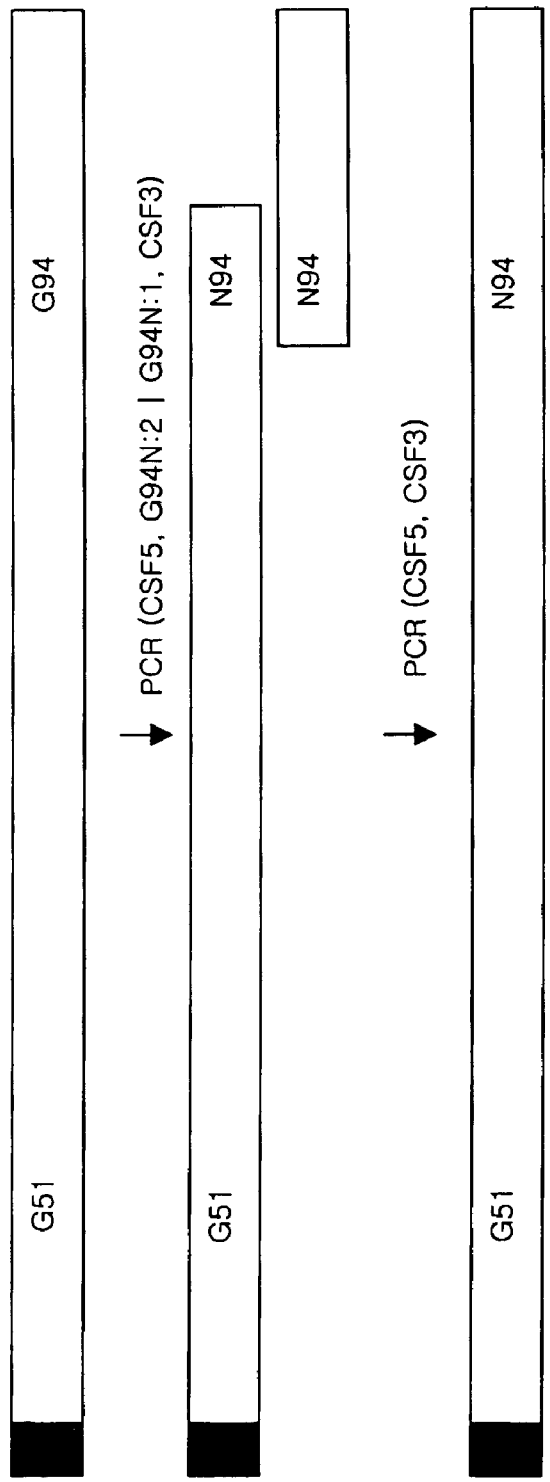
FIG. 4 shows a procedure for modifying the 94th glycine residue of natural human G-CSF with asparagine.

(2) Preparation of Human G-CSF Isoform With G94N Modification (FIG. 4)

The human G-CSF gene prepared in Example 1 was amplified by PCR using a primer set of CSF5 and G94N2 and another primer set of G94N1 and CSF3. The resulting DNA fragments were purified, and denatured with 0.2 M NaOH/2 mM EDTA. Using the denatured DNA fragments as templates, PCR was carried out with a primer set of CSF5 and CSF3 in order to produce a mutated human G-CSF gene having a modification of the 94th glycine residue to asparagine. As a result, as shown in FIG. 4, two DNA fragments carrying a codon corresponding to asparagine instead of glycine at the 94th amino acid position were obtained. After the two DNA fragments were added to a PCR reaction mixture, secondary PCR was carried out using a primer set of CSF5 and CSF3, resulting in production of a modified G-CSF-G94N gene with a modification of the 94th amino acid residue to asparagine, which can be additionally glycosylated.

Figure 5:
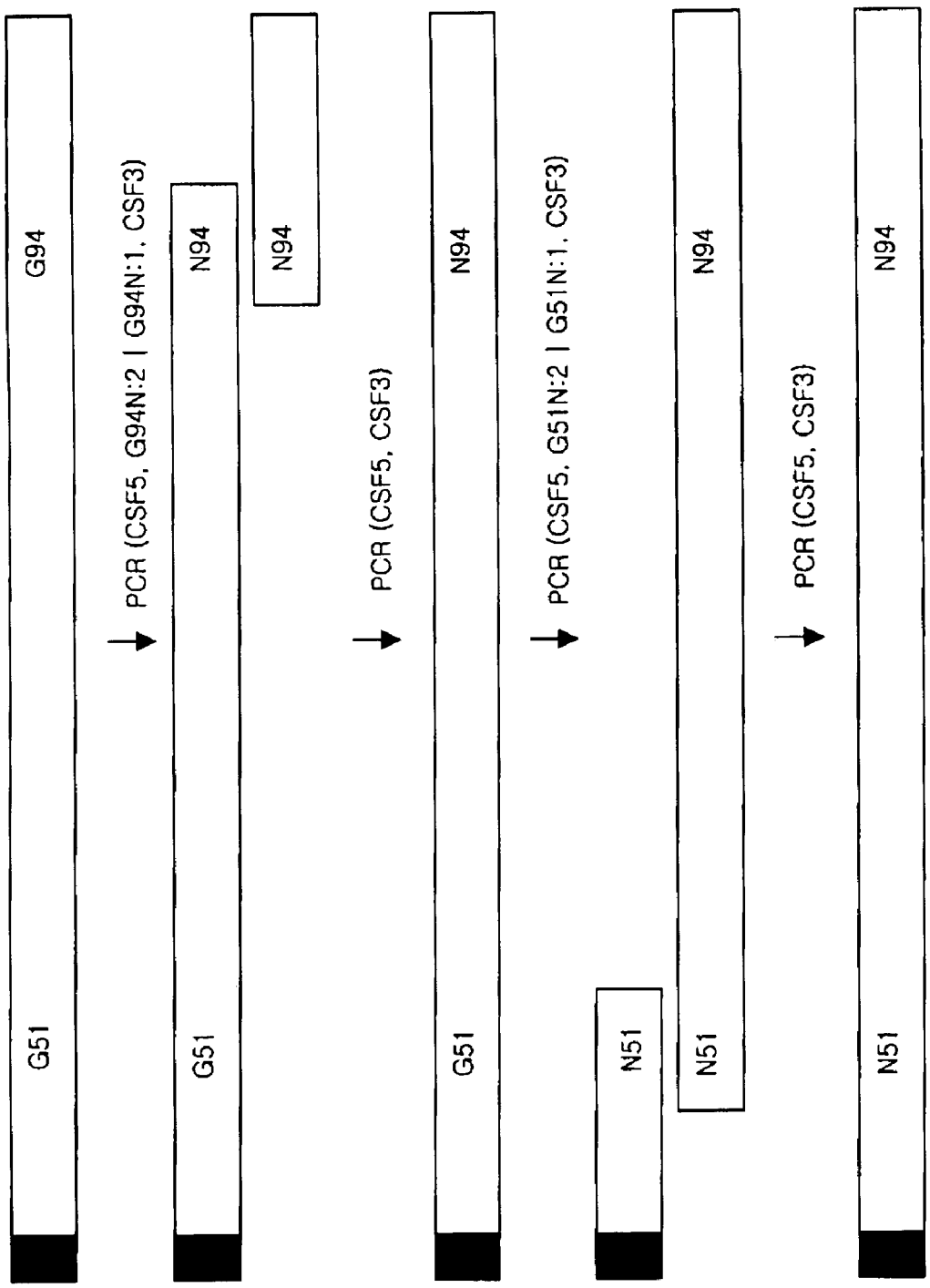
FIG. 5 shows a procedure for modifying both of the 51st and 94th glycine residues of natural human G-CSF with asparagine.

(3) Preparation of Human G-CSF Isoform With both G51N and G94N Modification (FIG. 5)

Using the modified G-CSF-G94N gene, a human G-CSF isoform with both G51N and G94N modification was prepared according to the same method as in preparing the modified G-CSF-G51N gene. As shown in FIG. 5, the 94th amino acid residue was modified first according to the same method as described in FIG. 4. Then, using the resulting DNA fragments as templates, the 51st amino acid residue was modified according to the same method as described in FIG. 3. As a result, a modified human G-CSF gene with both G51N and G94N modification was generated.

Figure 6:
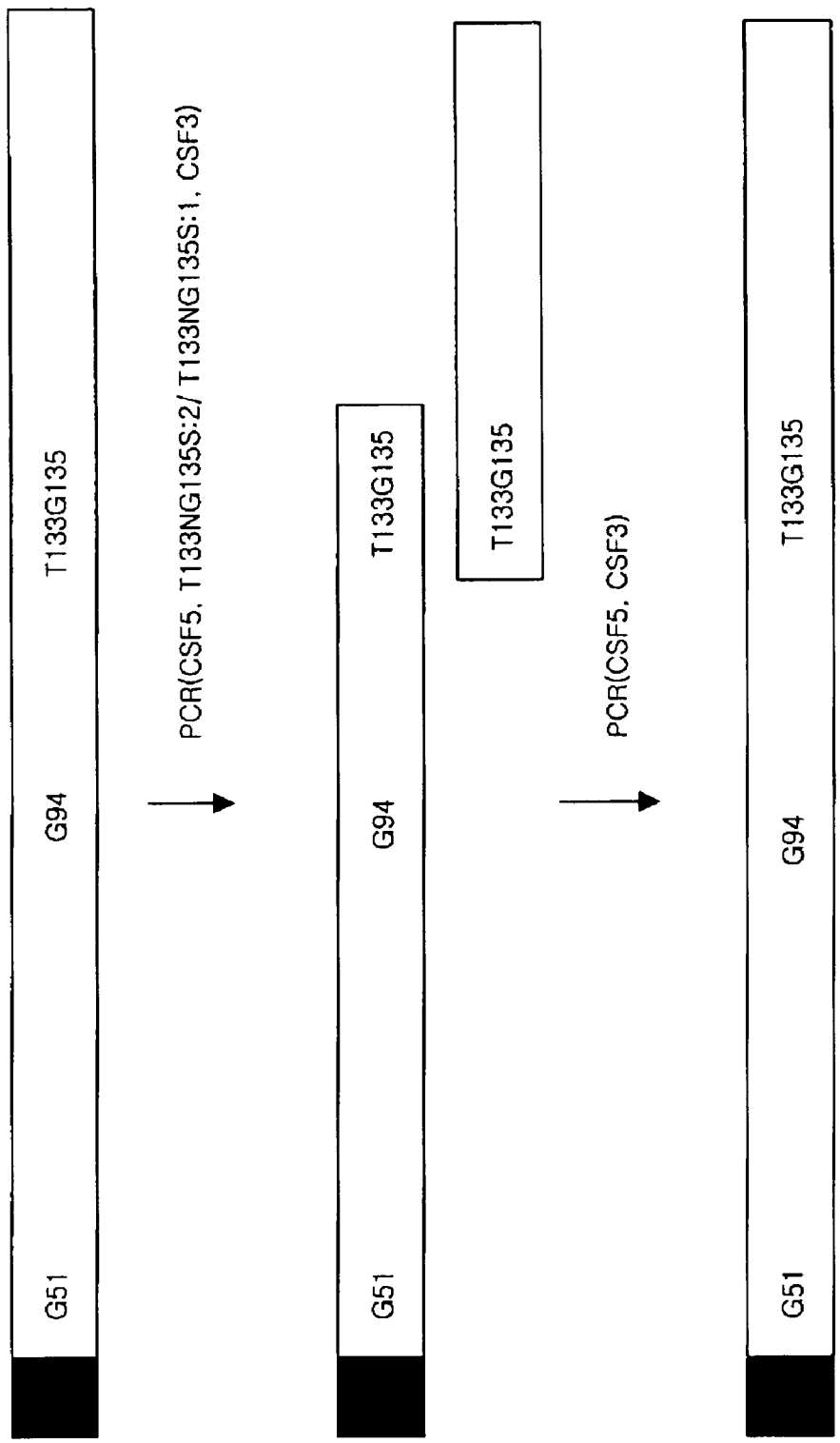
FIG. 6 shows a procedure for modifying the 133rd threonine and 135th glycine residues of natural human G-CSF with asparagine and serine, respectively.

(4) Preparation of Human G-CSF Isoform With both T133N and G135S Modifications (FIG. 6)

According to the same method as in preparing the modified G-CSF-G51N gene, human G-CSF gene was amplified by PCR using a primer set of CSF5 and T133NG135S:2 and another primer set of T133NG135S:1 and CSF3.

The resulting DNA fragments were purified, and denatured with 0.2 M NaOH/2 mM EDTA. Using the denatured DNA fragments as templates, PCR was carried out with a primer set of CSF5 and CSF3 in order to produce a modified human G-CSF gene having two modifications of the 133rd threonine residue and 135th glycine residue with asparagine and serine, respectively, wherein the O-linked glycosylation site was changed to an N-linked glycosylation site. As a result, a modified G-CSF-T133NG135S gene was produced.

Figure 7:
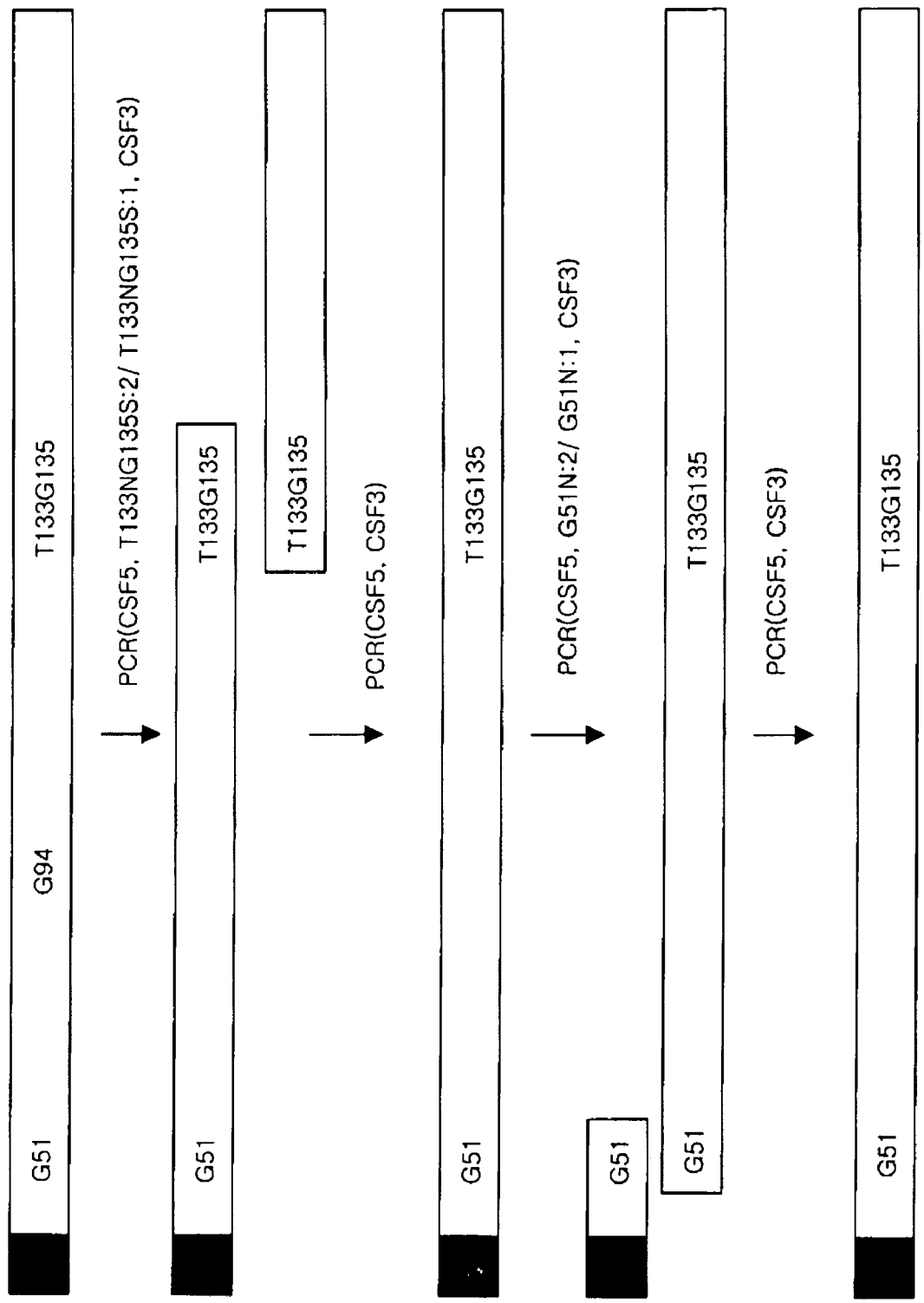
FIG. 7 shows a procedure for modifying Gly-51, Thr-133 and Gly-135 of natural human G-CSF with asparagine, asparagine and serine, respectively.

(5) Preparation of Human G-CSF Isoform With all of G51N, T133N and G135S Modifications (FIG. 7)

Using the modified G-CSF-T133NG135S gene, a modified human G-CSF gene with all of G51N, T133N and G135S modifications was prepared according to the same method as in preparing the modified G-CSF-G51N gene.

EXAMPLE 4

Expression of the Human G-CSF Isoform in CHO Cells

CHO cells (DG44) were cultured in a 60-mm culture dish, and grown to 40-80% confluency, that is, up to a density of 1-4×10$^5$ cells. After well mixing 3 μl of Superfectin reagent produced by the BM company with 97 μl of the culture medium (α-MEM, serum and antibiotic-free), the prepared expression vector DNA for a human G-CSF isoform (>0.1 μg/μl, about 2 μg) and the pLTRdhfr26 vector (ATCC37295, 0.2 μg) containing the mouse DHFR gene was added to the mixture. After incubation at room temperature for 5-10 min, the reaction mixture was added to the prepared cells. After one day, the cells were referred with dialyzed 10% FBS-containing α-MEM containing 200 μg/ml of hygromycine, and further cultured for about 7-10 days. Cells stably transfected with the human G-CSF isoform were selected from the hygromycine (200 μg/ml)-containing medium. Each of the selected cell lines was cultured and evaluated for expression of the human G-CSF isoform using the Quantikine human G-CSF immunoassay kit (Catalog No. DCS50, R&D systems). As a result, the human G-CSF isoform was found to be produced in the cell lines.

EXAMPLE 5

Purification of the Expressed Human G-CSF Isoform

Figure 8:
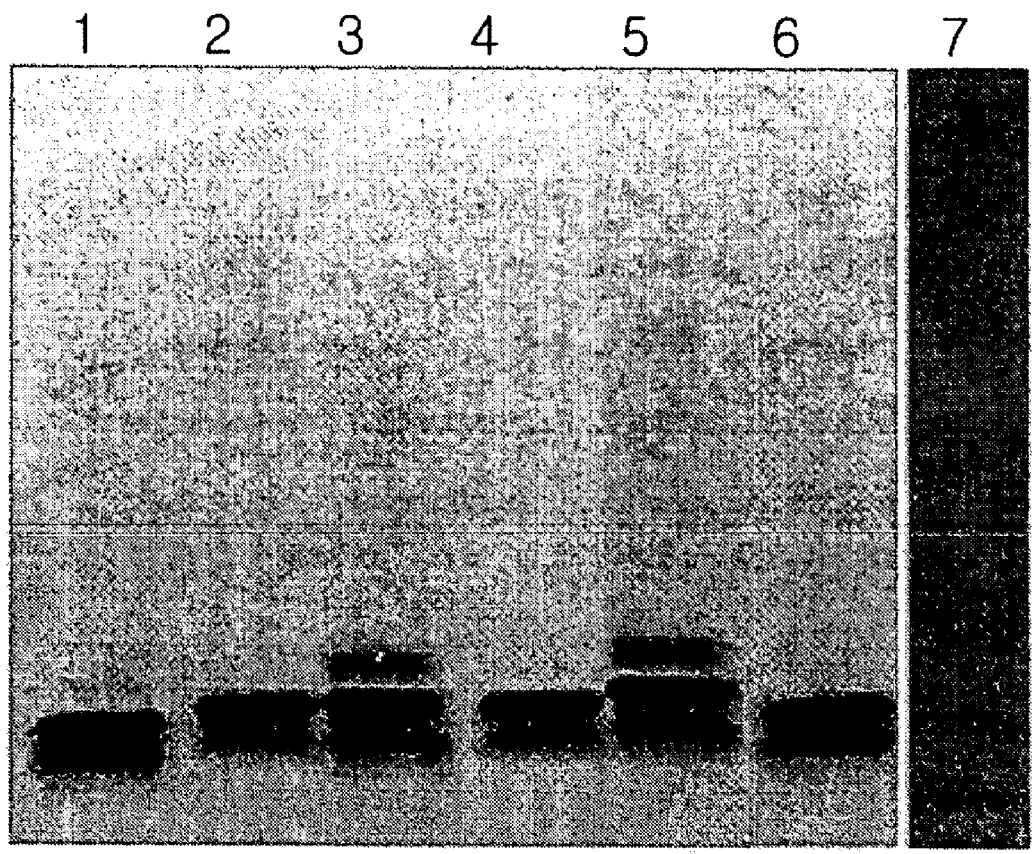
FIG. 8 is a photograph showing a result of Western blotting of the human G-CSF isoforms (lane 1: wild-type human G-CSF; lane 2: G51N isoform; lane 3: G51N/G94N isoform; lane 4: G94N isoform; lane 5: G51N/T133NG135S isoform; lane 6: T133NG135S isoform; and lane 7: size marker), wherein a goat polyclonal antibody to human G-CSF was used as the primary antibody, and mouse anti-goat HRP-conjugated polyclonal antibody was used as the secondary antibody.

The human G-CSF isoform expressed in CHO cells was purified as follows. The culture supernatant was concentrated using Millipore's Centriprep (Mw Cut 10,000). From the concentrate, the expressed human G-CSF isoform was purified by metal affinity chromatography using Invitrogen's ProBond Purification System, and analyzed by Western blotting. The results are given in FIG. 8.

EXAMPLE 6

Pharmacokinetic Assay in Rats

Figure 9:
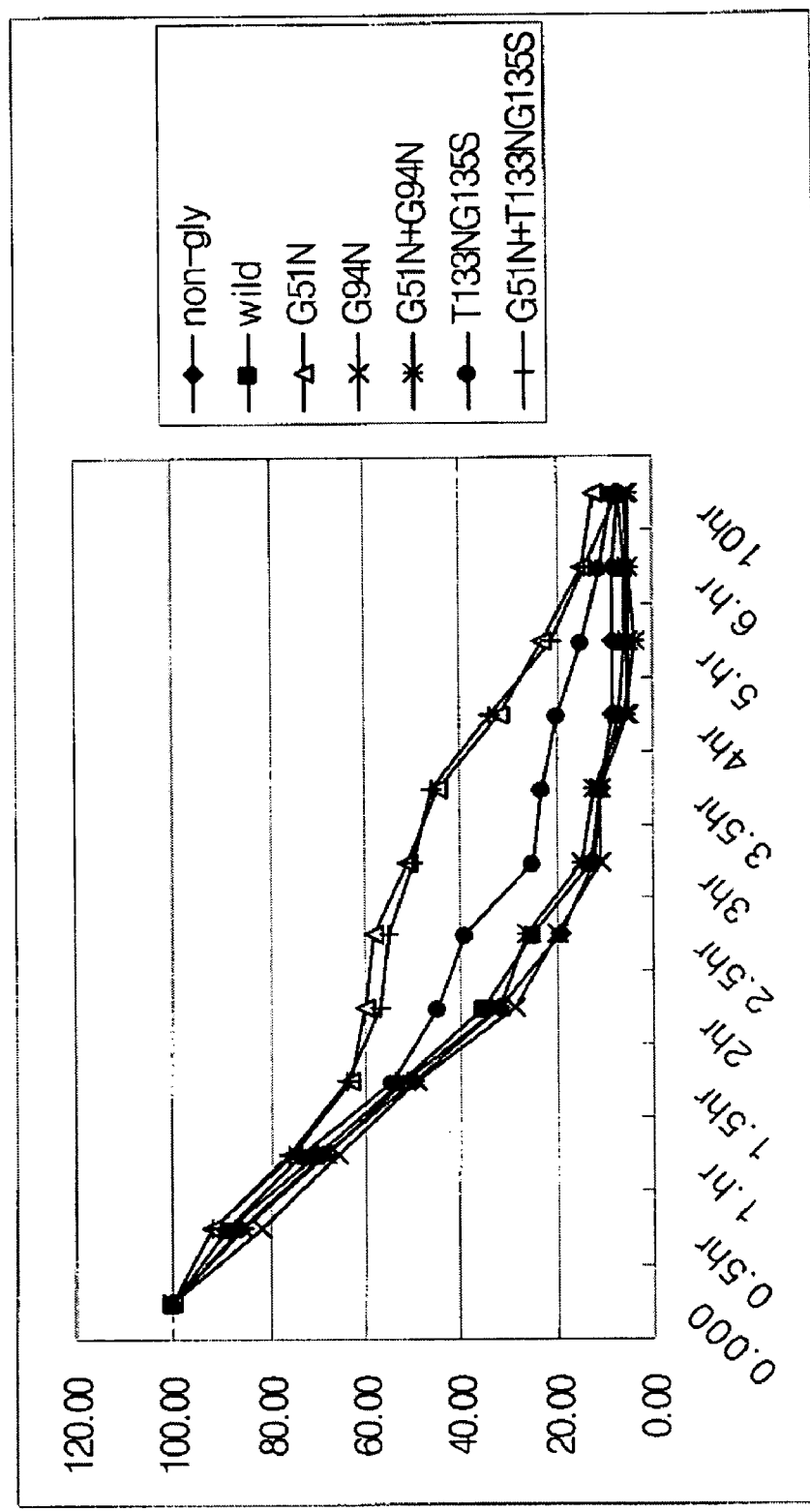
FIG. 9 is a graph showing blood levels of the human G-CSF isoforms in rats according to time.

In order to investigate whether the human G-CSF isoforms have prolonged half-life in vivo, a pharmacokinetic assay was performed in Sprague-Dawley rat subjects. The human G-CSF isoforms were administered intraveneously at a dosage of 100 μg/kg body weight, wherein each group was composed of four rats. Bleeding was carried out at intervals of 30 min, and blood levels of the human G-CSF isoforms were measured using the Quantikine Human G-CSF immunoassay kit (R&D systems). The results are given in FIG. 9. As shown in FIG. 9, some of the human G-CSF isoforms were found to have improved in vivo stability with comparison to natural G-CSF.

INDUSTRIAL APPLICABILITY

As described hereinbefore, the glycosylated human G-CSF isoforms according to the present invention have improved in vivo stability. Therefore, the human G-CSF isoforms can be clinically applied at a lower dosage and less frequently than the conventionally used human G-CSF.

What is claimed is:

1. A human G-CSF isoform having a modification of the $51^{st}$ glycine residue to asparagine, or of the $51^{st}$ glycine residue to asparagine and of the $94^{th}$ glycine residue to asparagine in the amino acid sequence of SEQ ID NO: 20.

2. A gene encoding a human G-CSF isoform having a modification of the $51^{st}$ glycine residue to asparagine, or of the $51^{st}$ glycine residue to asparagine and of the $94^{th}$ glycine residue to asparagine in the amino acid sequence of SEQ ID NO: 20.

3. A method of preparing a glycosylated human G-CSF isoform, comprising the steps of:

culturing a eukaryotic host cell transformed or transfected with an expression vector carrying the gene encoding a human G-CSF isoform of claim 2, and isolating the glycosylated human G-CSF isoform from the culture supernatant or cell lysates.

4. A pharmaceutical composition comprising a glycosylated human G-CSF isoform prepared by additional glycosylation of the human G-CSF isoform of claim 1 and a pharmaceutically acceptable carrier.

* * * * *

SEQUENCE LISTING

```
<160> NUMBER OF SEQ ID NOS: 12

<210> SEQ ID NO 1
<211> LENGTH: 33
<212> TYPE: DNA
<213> ORGANISM: Artificial Sequence
<220> FEATURE:
<223> OTHER INFORMATION: primer

<400> SEQUENCE: 1
```

```
atgggggtt ctcatcatca tcatcatcat ggg                               33

<210> SEQ ID NO 2
<211> LENGTH: 36
<212> TYPE: DNA
<213> ORGANISM: Artificial Sequence
<220> FEATURE:
<223> OTHER INFORMATION: primer

<400> SEQUENCE: 2
catcatcatc atcatcatgg ggacgatgac gataag                           36

<210> SEQ ID NO 3
<211> LENGTH: 30
<212> TYPE: DNA
<213> ORGANISM: Artificial Sequence
<220> FEATURE:
<223> OTHER INFORMATION: primer

<400> SEQUENCE: 3 acccccatg gcttcctgca ctgtccagtg                                   30

<210> SEQ ID NO 4
<211> LENGTH: 36
<212> TYPE: DNA
<213> ORGANISM: Artificial Sequence
<220> FEATURE:
<223> OTHER INFORMATION: primer

<400> SEQUENCE: 4
ggggacgatg acgataagac cccctgggc cctgcc                            36

<210> SEQ ID NO 5
<211> LENGTH: 39
<212> TYPE: DNA
<213> ORGANISM: Artificial Sequence
<220> FEATURE:
<223> OTHER INFORMATION: primer

<400> SEQUENCE: 5
gaggagctgg tgctgctcaa ccactctctg gcatcccc                         39

<210> SEQ ID NO 6
<211> LENGTH: 39
<212> TYPE: DNA
<213> ORGANISM: Artificial Sequence
<220> FEATURE:
<223> OTHER INFORMATION: primer

<400> SEQUENCE: 6
ggggatgccc agagagtggt tgagcagcac cagctcctc                        39

<210> SEQ ID NO 7
<211> LENGTH: 42
<212> TYPE: DNA
<213> ORGANISM: Artificial Sequence
<220> FEATURE:
<223> OTHER INFORMATION: primer

<400> SEQUENCE: 7
ctcctgcagg ccctggaaaa catctccccc gagttgggtc cc                    42

<210> SEQ ID NO 8
<211> LENGTH: 42
<212> TYPE: DNA
<213> ORGANISM: Artificial Sequence
```

-continued

```
<220> FEATURE:
<223> OTHER INFORMATION: primer

<400> SEQUENCE: 8
gggacccaac tcggggaga tgttttccag ggcctgcagg ag                          42

<210> SEQ ID NO 9
<211> LENGTH: 39
<212> TYPE: DNA
<213> ORGANISM: Artificial Sequence
<220> FEATURE:
<223> OTHER INFORMATION: primer

<400> SEQUENCE: 9
cctgccctgc agcccaacca gagcgccatg ccggccttc                             39

<210> SEQ ID NO 10
<211> LENGTH: 39
<212> TYPE: DNA
<213> ORGANISM: Artificial Sequence
<220> FEATURE:
<223> OTHER INFORMATION: primer

<400> SEQUENCE: 10
gaaggccggc atggcgctct ggttgggctg cagggcagg                             39

<210> SEQ ID NO 11
<211> LENGTH: 31
<212> TYPE: DNA
<213> ORGANISM: Artificial Sequence
<220> FEATURE:
<223> OTHER INFORMATION: primer

<400> SEQUENCE: 11
tcccaagctt atggctggac ctgccaccca g                                    31

<210> SEQ ID NO 12
<211> LENGTH: 32
<212> TYPE: DNA
<213> ORGANISM: Artificial Sequence
<220> FEATURE:
<223> OTHER INFORMATION: primer

<400> SEQUENCE: 12
tgggatcctc agggctgggc aaggtggcgt ag                                   32
```